US010379535B2

(12) United States Patent
Migneco et al.

(10) Patent No.: US 10,379,535 B2
(45) Date of Patent: Aug. 13, 2019

(54) DROWSINESS SENSING SYSTEM (71) Applicant: Lear Corporation, Southfield, MI (US)

(72) Inventors: Francesco Migneco, Salene, MI (US); David Gallagher, Sterling Heights, MI (US)

(73) Assignee: Lear Corporation, Southfield, MI (US)

( * ) Notice: Subject to any disclaimer, the term of this patent is extended or adjusted under 35 U.S.C. 154(b) by 0 days.

(21) Appl. No.: 15/792,085

(22) Filed: Oct. 24, 2017

(65) Prior Publication Data

US 2019/0121356 A1    Apr. 25, 2019

(51) Int. Cl.
| | |
|---|---|
| *G01C 22/00* | (2006.01) |
| *G05D 1/00* | (2006.01) |
| *A61B 5/00* | (2006.01) |
| *A61B 5/0205* | (2006.01) |
| *A61B 5/18* | (2006.01) |
| *B60W 30/09* | (2012.01) |

(Continued)

(52) U.S. Cl.
CPC ......... *G05D 1/0061* (2013.01); *A61B 5/0077* (2013.01); *A61B 5/0205* (2013.01); *A61B 5/18* (2013.01); *A61B 5/6893* (2013.01); *A61B 5/7278* (2013.01); *A61B 5/746* (2013.01); *A61B 5/7455* (2013.01); *B60W 30/09* (2013.01); *B60W 50/14* (2013.01); *G05D 1/0088* (2013.01); *A61B 5/024* (2013.01); *A61B 5/02405* (2013.01); *A61B 5/0531* (2013.01); *A61B 2560/0242* (2013.01); *B60W 2050/143* (2013.01); *B60W 2420/42* (2013.01); *B60W 2422/00* (2013.01); *B60W 2540/26* (2013.01)

(58) Field of Classification Search
CPC .... G05D 1/0061; A61B 5/007; A61B 5/0205; A61B 5/18; A61B 5/6893; A61B 5/7278; A61B 5/7455; A61B 5/746; A61B 5/0476; B60W 40/08
USPC ........................................... 701/23; 340/576
See application file for complete search history.

(56) References Cited

U.S. PATENT DOCUMENTS

| | | | |
|---|---|---|---|
| 6,366,207 | B1 | 4/2002 | Murphy |
| 7,138,922 | B2 | 11/2006 | Strumolo et al. |

(Continued)

FOREIGN PATENT DOCUMENTS

| | | |
|---|---|---|
| CN | 204147427 U | 2/2015 |
| DE | 10126224 A1 | 12/2002 |

(Continued)

OTHER PUBLICATIONS

Burgess, M., "This car headrest monitors your brain waves to stop you falling asleep at the wheel", WIRED Online Article, Jan. 15, 2017, 9 pgs.

(Continued)

*Primary Examiner* — Mahmoud S Ismail
(74) *Attorney, Agent, or Firm* — Brooks Kushman P.C.

(57) ABSTRACT

A system includes an electro-dermal potential sensing system to sense electro-dermal potential of a person and configured to output an electro-dermal potential signal, as well as at least one physiological sensor to measure at least one physiological state and output at least one physiological signal. The system also includes a controller to receive the electro-dermal potential signal from the electro-dermal potential sensing system and the at least one physiological signal to determine a drowsiness state of the person.

20 Claims, 4 Drawing Sheets

(51) Int. Cl.
*B60W 50/14* (2012.01)
*G08B 23/00* (2006.01)
*A61B 5/024* (2006.01)
*A61B 5/053* (2006.01)

(56) References Cited

U.S. PATENT DOCUMENTS

| | | | |
|---|---|---|---|
| 7,437,219 | B2 | 10/2008 | Bos |
| 7,774,052 | B2 | 8/2010 | Burton et al. |
| 8,698,639 | B2 | 4/2014 | Fung et al. |
| 8,903,494 | B2 | 12/2014 | Goldwasser et al. |
| 9,002,458 | B2 | 4/2015 | Pal et al. |
| 9,014,811 | B2 | 4/2015 | Pal et al. |
| 9,124,955 | B2 | 9/2015 | Geva et al. |
| 9,135,803 | B1 | 9/2015 | Fields et al. |
| 9,149,236 | B2 | 10/2015 | Chun et al. |
| 9,233,244 | B2 | 1/2016 | Pal et al. |
| 9,272,689 | B2 | 3/2016 | Fung et al. |
| 9,298,985 | B2 | 3/2016 | Krueger |
| 9,302,584 | B2 | 4/2016 | Walsh et al. |
| 9,389,595 | B2 | 7/2016 | Caskey et al. |
| 9,440,646 | B2 | 9/2016 | Fung et al. |
| 9,460,601 | B2 | 10/2016 | Mimar |
| 9,463,794 | B1 | 10/2016 | Silver et al. |
| 9,475,502 | B2 | 10/2016 | Fung et al. |
| 9,536,411 | B2 | 1/2017 | Foley et al. |
| 9,539,944 | B2 | 1/2017 | Tzirkel-Hancock et al. |
| 9,956,963 | B2 | 5/2018 | Vijaya Kumar et al. |
| 2006/0015000 | A1 | 1/2006 | Kim |
| 2009/0174573 | A1 | 7/2009 | Smith |
| 2012/0116198 | A1 | 5/2012 | Veen et al. |
| 2012/0259181 | A1 | 10/2012 | Fujita et al. |
| 2012/0330173 | A1 | 12/2012 | Park et al. |
| 2013/0325202 | A1 | 12/2013 | Howard et al. |
| 2014/0136450 | A1 | 5/2014 | Lee |
| 2014/0139655 | A1 | 5/2014 | Mimar |
| 2015/0032382 | A1 | 1/2015 | Lee et al. |
| 2015/0313475 | A1 | 11/2015 | Benson et al. |
| 2015/0328985 | A1 | 11/2015 | Kim et al. |
| 2015/0360608 | A1 | 12/2015 | Tzirkel-Hancock et al. |
| 2015/0379362 | A1* | 12/2015 | Calmes ............... G06K 9/2036 348/136 |
| 2016/0090097 | A1* | 3/2016 | Grube ................ B60W 40/08 340/576 |
| 2016/0133151 | A1 | 5/2016 | O'Dowd et al. |
| 2016/0260343 | A1 | 9/2016 | Resl |
| 2016/0292988 | A1 | 10/2016 | McCleary et al. |
| 2017/0068245 | A1 | 3/2017 | Scofield et al. |
| 2017/0071525 | A1* | 3/2017 | Lin ....................... A61B 5/18 |
| 2017/0136842 | A1 | 5/2017 | Anderson et al. |
| 2017/0188927 | A1 | 7/2017 | Nakashima et al. |
| 2017/0196497 | A1 | 7/2017 | Ray et al. |
| 2017/0311831 | A1* | 11/2017 | Freer .................. A61B 5/04014 |
| 2017/0351812 | A1 | 12/2017 | Green et al. |
| 2017/0355377 | A1* | 12/2017 | Vijaya Kumar ...... B60W 40/08 |
| 2017/0360363 | A1* | 12/2017 | Fonseca ............. A61B 5/7264 |
| 2017/0367635 | A1 | 12/2017 | Hur et al. |
| 2018/0008145 | A1 | 1/2018 | Freer et al. |
| 2018/0136191 | A1 | 5/2018 | Asvadi et al. |
| 2018/0143006 | A1 | 5/2018 | White |
| 2018/0189681 | A1 | 7/2018 | Harrivel et al. |
| 2018/0197636 | A1 | 7/2018 | Firminger et al. |
| 2018/0229674 | A1 | 8/2018 | Heinrich et al. |
| 2018/0276362 | A1 | 9/2018 | Baughman et al. |

FOREIGN PATENT DOCUMENTS

| | | |
|---|---|---|
| DE | 102012002037 B4 | 3/2015 |
| EP | 2308559 A2 | 4/2011 |
| FR | 2880166 A1 | 6/2006 |
| JP | 2010241963 A | 10/2010 |
| WO | 2007090896 A1 | 8/2007 |

OTHER PUBLICATIONS

Wess, J., "Prototype Testing of EEG Headrests", Freer Logic Online Article—Comments Off on Prototype Testing of EEG Headrests, Aug. 3, 2017, 2 pgs.

Lisetti, C., "Affective Intelligent Car Interfaces with Emotion Recognition", In Proceedings of 11th International Conference on Human Computer Interaction, Las Vegas, NV, USA, Jul. 2005.

* cited by examiner

DROWSINESS SENSING SYSTEM

TECHNICAL FIELD

The present disclosure relates to systems with sensors to provide sensed information about a person's drowsiness state.

BACKGROUND

It is advantageous to be able to detect a person's drowsiness. For instance, driving of a motor vehicle while drowsy, which is a type of driver error, is a significant cause of preventable road accidents. Vehicle systems that assist in warning a driver of drowsiness or take action in such an occurrence may reduce the number of such accidents or attempt to mitigate damage caused by driver drowsiness.

SUMMARY

A system includes an electro-dermal potential sensing system to sense electro-dermal potential of a person and configured to output an electro-dermal potential signal. At least one physiological sensor measures at least one physiological parameter of the person and outputs at least one physiological signal. A controller receives the electro-dermal potential signal from the electro-dermal potential sensing system and the at least one physiological signal to determine a drowsiness state of the person.

In an example embodiment, the system includes a vehicle seat, the person is a driver seated in the seat, and the electro-dermal potential sensing system is at least partially integrated into the seat.

In an example embodiment, the at least one physiological parameter is one or more of heart rate, respiration rate, heart rate variability, CRS (Cardiorespiratory Coupling/Synchrogram).

In an example embodiment, the control signal is to adjust operation of an adaptive braking system in the vehicle based on the determined drowsiness state of the driver exceeding a drowsiness threshold.

In an example embodiment, the electro-dermal potential system includes a plurality of contactless sensors mounted in the seat; wherein the seat includes a head rest. The plurality of contactless sensors includes one or more headrest sensors mounted in the headrest to measure electro-dermal potential at a head of the driver.

In an example embodiment, the seat includes a driver warning device to indicate to the driver that the control signal representing drowsiness is output from the controller.

In an example embodiment, the controller measures driver drowsiness based on individual frequency components in the electro-dermal potential signal.

In an example embodiment, the controller quantifies a drowsiness state level based on the electro-dermal potential signal and the physiological signal and outputs a level signal to adjust a time-to-impact variable in an object avoidance calculation.

In an example embodiment, a camera to sense an image of the driver and produce a video output, and wherein the controller uses the video output to detect drowsiness indicators. The controller uses the drowsiness indicators to calculate the drowsiness state level of the driver.

In an example embodiment, the controller quantifies a drowsiness state level based on the electro-dermal potential signal and the physiological signal and controls a driver alert based on the drowsiness state level. When the drowsiness state level exceeds the drowsiness threshold, the controller activates a driver alarm or a vibration in the seat.

In an example embodiment, an external sensor to detect objects external to the vehicle, the external sensor producing object detection signals using a sensor range. The controller increases the sensor range when the drowsiness state exceeds the drowsiness threshold.

In an example embodiment, the controller receives sensor signals from at least one of an internal video signal, an external camera signal, a navigational position signal, a vehicle speed signal, or combinations thereof. The controller uses internal video signal, an external camera signal, the navigational position signal, the vehicle speed signal and the electro-dermal potential signal to determine a false drowsiness state of the driver.

In an example embodiment, the controller switches vehicle operation from a manual mode to an autonomous driving mode.

A vehicle system is described with a vehicle environmental sensor system configured to sense external objects around the vehicle and output an external sensor signal and a seat configured to support an occupant and to be mounted in a vehicle. An electro-dermal potential system is at least partially integrated into the seat and configured to output an electro-dermal potential signal. A physiological sensor is in the vehicle and is configured to measure at least one of a heart rate, a respiration rate, or both of the occupant in the seat and output a physiological signal. A controller is configured to receive the electro-dermal potential signal from the electro-dermal potential system, the physiological signal from the electro-dermal potential system and the external sensor signal from the vehicle environmental sensor system and to output a control signal using the electro-dermal potential signal, the physiological signal and the external sensor signal to adjust operation of the vehicle environmental sensor system in the vehicle.

In an example embodiment, the electro-dermal potential system includes a plurality of contactless sensors mounted in the seat. The contactless sensors are positioned adjacent the seat occupant by are not in direct physical contact with the seat occupant.

In an example embodiment, the vehicle environmental sensor system includes a detection and ranging system with a range setting to sense objects outside the vehicle including a position and a range of an external object and the external sensor signal includes the position and range of the external object. The range setting is adjusted by the controller based on the electro-dermal potential signal, the physiological signal and the external sensor signal.

In an example embodiment, the vehicle environmental sensor system includes a light sensor, a LIDAR, a camera, a radio frequency sensor, RADAR or combinations thereof.

In an example embodiment, a collision avoidance system having a trigger time based on the control signal from the controller. The collision avoidance system triggers an avoidance action based on the trigger time. The collision avoidance system has a first trigger time when the drowsiness state is not detected, a second trigger time when the drowsiness state increases, and a third trigger time with the drowsiness state exceeding the drowsiness threshold. The second trigger time is less than the first trigger time. The third trigger time is the shortest. The third trigger time may change the vehicle driving mode from manual to autonomous for vehicles with autonomous capability.

Any of the above examples may be combined with each other to form additional embodiments of the present disclo-

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The present disclosure is generally directed to a seat sensor that can be embedded in any part of the foam, trim, headrest, frame or a combination thereof of a vehicle seat. At least one of the sensors determines the electro-dermal potential (EDP) originating primarily from brain cortical activity. Such EDP sensing can be contact or non-contact (e.g., field sensing) and can also sense muscle activity and skin characteristics. This will reveal high-level central nervous system (CNS) functions such as drowsiness or distraction. The systems described herein employ real-time processing of the electrical potential fluctuations, e.g., comparing various frequency bands of the sensed signal with respect to each other. These can act as the primary brain activity quantitative classifiers. The present systems may use the sensed signals along with other sensor information to determine false positives of drowsiness based on the sensed EDP signal. This system, through the acquisition of the appropriate physiological metrics, and use of a software algorithm, is capable of determining if the occupant is distracted and not attentive to the road task of the moment while correcting for false positive indications of drowsiness.

A contactless EDP sensing system can be integrated with the seat including one or more sensors embedded in any part of the seat, e.g., the foam, the trim, the headrest or a combination thereof. The contactless EDP sensing system can be supplemented by appropriate physiological metrics (heart rate, HRV, CRS (Cardiorespiratory Coupling/Synchrogram), breathing rate, and the like for both standard and complex non-linear dynamics) of the seat occupant, e.g., the driver. A controller can receive the relevant signals and determine if the occupant is drowsy and therefore if attention and reaction time is affected. The controller can be adapted to individual occupants using an automated user-specific calibration This system can also comprise inward cameras, strategically positioned to look at the driver. Inward cameras can be used in the drowsiness detection system to achieve sensor fusion and increase specificity and accuracy of the drowsiness detection. The camera generates multiple images of the occupant, which can be analyzed to determine additional occupant metrics. The metrics can include head position, a blink rate, pupil dilation, eye position, fixation, gaze patterns, eyelid closure, head movement facial expression, and the like.

The use of various metrics from different sources provides an objective quantification of the occupant's drowsiness. The drowsiness quantification can be combined with other data in the vehicle to prevent false indications of drowsiness, e.g., vehicle performance, driving environment and the like. If the drowsiness quantification exceeds a drowsiness threshold, then the vehicle may automatically trigger countermeasures, e.g., alerts, alarms, collision avoidance and the like. If the drowsiness/concentration status of the driver is quantified, the vehicle can change reaction times of the collision avoidance system, e.g., the adaptive braking system, to optimize the response of the system itself in view of the driver condition.

Figure 1:
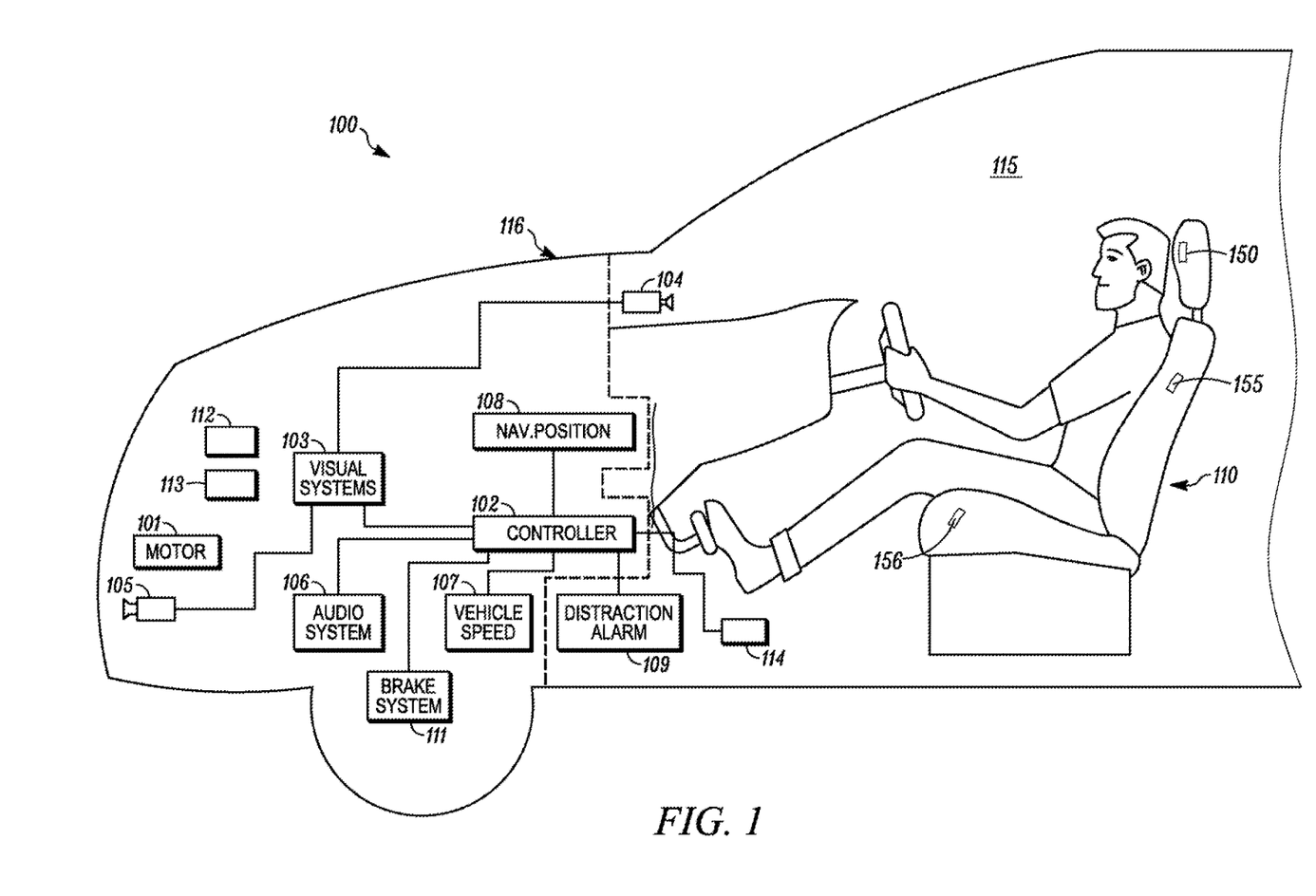
FIG. 1 is a schematic view of a vehicle according to an example embodiment.

FIG. 1 shows a vehicle 100 including a cabin 115 and an engine bay 116, which can be forward of the cabin 115. The engine bay 116 houses a motor 101 that provides motive power to the vehicle. A controller 102 includes an electrical signal processor adapted to execute tasks, which can be stored in a memory. The tasks can process sensed signals according to rules loaded into the controller 102. The sensed data can be stored in memory associated with the controller 102.

Visual systems 103 are provided to receive instructions from the controller 102 and produce visual displays in the vehicle, e.g., in the cabin on display screens, the dashboard, a mobile electronic device associated with the vehicle. The displays produced by the visual systems can be images sensed by and internal camera 104, an external camera 105, collision warnings, distraction warnings and the like. The visual system 103 can process the image data from the cameras 104, 105 before providing, the image data to the controller 102. The visual system 103 can process in images to identify objects and the position of the driver in an example embodiment. This data can be provided to the controller 102.

An audio system 104 can be part of a head unit in the vehicle. The audio system 104 can sense audio in the cabin 115 and output audio into the cabin, e.g., using multiple speakers. The audio output from the audio system 104 can be warnings as described herein based on instruction from the controller 102. The audio warnings can be spoken words or tones to indicate driver distraction, change in settings, imminent danger, activation of collision warning system or combinations thereof.

A vehicle speed sensor 107 is provided to detect the speed of the vehicle and provide a speed signal to the controller 102.

A navigational position system 108 detects the position of the vehicle by receipt of satellite signals or ground based position signals. The navigational position system 108 can include a global navigation satellite system (GNSS) such as Global Positioning System (GPS), Beidou, COMPASS, Galileo, GLONASS, Indian Regional Navigational Satellite System (IRNSS), or QZSS. The navigational system can include a receiver that receives differential correction signals in North American from the FAA's WAAS system. The navigational position system 108 provides accurate position of the vehicle to the controller 102.

A distraction alarm 109 is positioned in the cabin. The distraction alarm 109 can include mechanical alarms like vibration devices that can be positioned in the steering wheel or the seat. The distraction alarm 109 can be a signal to vibrate a mobile electronic device associated with the vehicle and a passenger in the vehicle.

A vehicle seat 110 is position in the cabin 115 and is configured to support a person, e.g., a driver or a passenger. The seal 110 can include a plurality of sensors 150, 155, 156 to detect various biometric characteristics of the person. The sensors 150 can be contactless and can sense EDP adjacent the head of the seated person. The sensors 155 and 156 can detect other biometric information. The sensors 155, 156 can sense the heart rate of the occupant of the seat in an example embodiment. The sensors 155, 156 can sense the breath rate of the occupant of the seat in an example embodiment. The sensed EDP data from the sensors 150 can be combined with either or both of the sensed hear rate and sensed breath rate from the sensors 155, 156 to detect and quantify drowsiness of the occupant, particularly, the driver, in the seat 110. In an example, the sensors 155, 156 can sense muscle movement to be used in determining drowsiness of the seat occupant. In an example, the sensors 155, 156 can sense EDP of the seat occupant to be used in determining drowsiness of the seat occupant.

A brake system 111 is provided to brake the wheels of the vehicle. The brake system 111 can be activated by the driver and can also be activated automatically by the controller, e.g., when distracted driving is detected, a crash is detected as imminent or an imminent danger is detected as described herein.

A laser sensing system 112, e.g., a LIDAR, is provided. The laser sensing system 112 emits light in pulses and detects the light returned after the light reflects of object external to the vehicle 100. The laser sensing system 112 can produce a digital three-dimensional representation of the external environment around the vehicle in the direction of the light pulses. The laser sensing system 112 can perform laser scanning to produce a representation around the vehicle. The external environment can include other vehicles, signs, and other objects. The representation or individually identified objects can be provided to the controller 102 for use in the vehicle as described herein.

A RADAR sensing system 113 is provided in the vehicle. The RADAR sensing system 113 emits radio frequency energy pulses and detects the returned pulses to identify objects around the vehicle or map the external environment. The representation or individually identified objects can be provided to the controller 102 for use in the vehicle as described herein.

Other typical vehicle systems may be included in the vehicle 100 but are not illustrated for clarity of the drawings. The controller 102 may provide inputs to these other systems.

Figure 2:
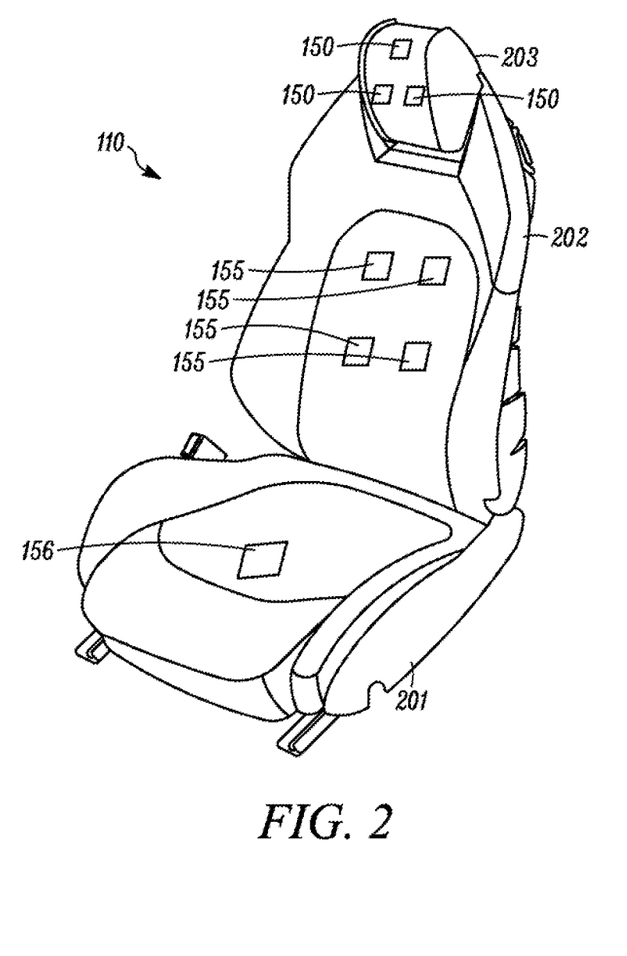
FIG. 2 is a schematic view of a vehicle seat with sensors therein according to an example embodiment.

FIG. 2 shows the vehicle seat 110 configured to be fixed in a cabin of a motor vehicle. The seat 110 is adapted to support a person on a base 201 in an upright position against a seat back 202. The base 201 is fixed to the floors in the vehicle cabin, e.g., by slidable rails. A headrest 203 may be positioned at the top of the seat back. Each of the base 201, seat back 202, and headrest 203 include a rigid frame, comfort layers on the frame and an external covering. A plurality of sensors 150, 155, 156 can be supported in the seat. A plurality of first sensors 150 may be positioned in the headrest 203 and adapted to sense EDP signals from the occupant of the seat. A plurality of second sensors 155 may be positioned in the seat back 202. The plurality of second sensors 155 may also sense EDP signals from the occupant. The plurality of second sensors 155 may include at least one sensor that does not sense EDP signals. One or more third sensors 156 are positioned in the seat base 201. The third sensors 156 may also sense EDP signals. The plurality of second sensors 155 may include at least one sensor that does not sense EDP signals and may, e.g., sense presence of a person in the seat and sense weight of the occupant of the seat. The sensors 150 develop raw EDP signals, which are filtered to produce analysis signals including frequency components relevant to EDP of the person in the seat while attenuating unrelated frequency components.

The drowsiness state of a person is monitored using the EDP at the head or torso of the occupant of the seat 110 by the sensors 150 in conjunction with the sensors 155, 156. The sensors 150 are positioned proximate to portions of the skin adjacent the head to develop raw EDP signals. The EDP raw signals can be filtered to produce at least one bandpass-filtered drowsiness state-indicating EDP signal representative of raw EDP signal magnitude within a predetermined frequency range as an indication of the drowsiness of the seated person.

Figure 3:
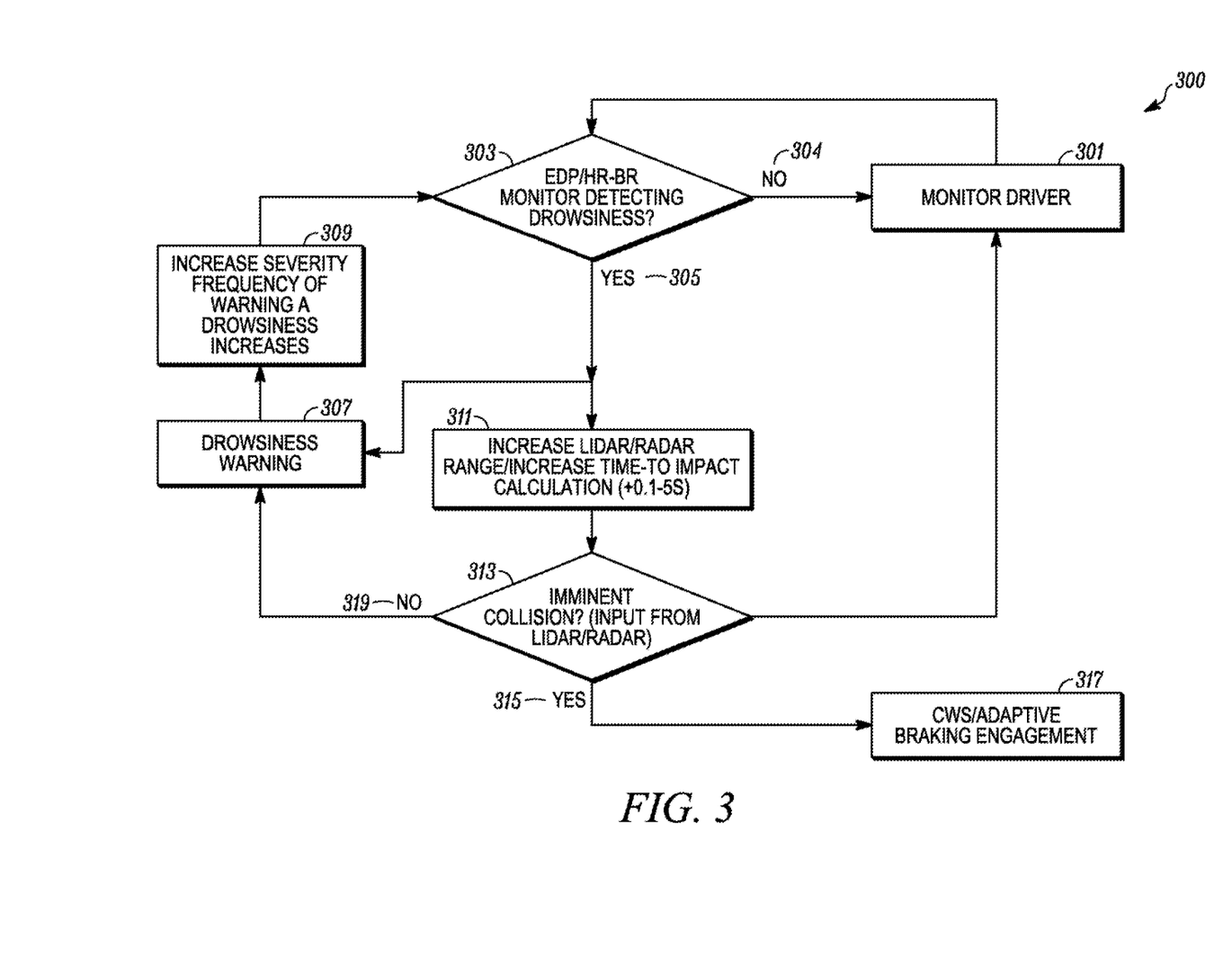
FIG. 3 is a functional block diagram of a vehicle system according to an example embodiment.

FIG. 3 shows process 300 that can be implemented in the vehicle 100 to sense a distracted state of the occupant of the seat. The process 300 can be implemented in the vehicle 100 in an example embodiment. At 301, the process starts by monitoring the driver (and occupant of a vehicle seat). The monitoring starts by sensing the presence of the driver in the seat. The monitoring can include sensing the EDP of the driver and a secondary physiological parameter of the driver. The EDP can by sensed, at least in part, about the head of the driver. The secondary physiological parameter can be heart rate or respiration rate.

At 303, both the EDP and the secondary physiological parameter are used to determine the drowsiness of the driver. The EDP can indicate brain waves that indicate drowsiness. The secondary physiological parameter can also indicate drowsiness, e.g., deep regular respiration, slowing respiration, slowing, heart rate and the like. At 304, if drowsiness is not detected, then the process returns to step 301 and continues monitoring the driver. The monitoring 301 and the detecting of drowsiness 303 can be performed simultaneously in some examples. If drowsiness is detected 305, then the process moves to issuing a drowsiness warning at 307. The drowsiness warning can be a visual indication on the dashboard or in a heads-up display, e.g., when a low level of drowsiness is detected. The vehicle may provide an audio warning, e.g., a tone or a spoken voice to warn the driver of the drowsiness state or level. Other forms of drowsiness warnings may be used. The seat may be equipped with a vibration device that vibrates the seat with varying patterns of the vibration. The steering wheel may include a vibration device to vibrate the steering wheel when drowsiness is detected.

The EDP signals can be separated into various sub-signals, e.g., at different frequencies, by using filters to allow certain divisions into sub-bands. These sub-bands may overlap in frequency ranges. A first sub-signal can be up to four hertz. A second sub-signal can be four hertz to seven hertz. A third sub-signal can be seven hertz to fourteen hertz. A fourth sub-signal can be fourteen hertz to about thirty hertz. A fifth sub-signal can be about thirty hertz to about one hundred hertz. Other sub-signals may overlap these ranges for the first through sixth sub-signals, e.g., from eight hertz to thirteen hertz. The relationships between these sub-signals can be used to determine whether the driver is drowsy. The patterns of the sub-signals or the ratios of multiple sub-signals to each other can be used to determine if a driver is drowsy.

At 309, the severity of the warning increases as the level of drowsiness increases. In an example, the visual warnings may be larger or brighter as the drowsiness level increases. The audio warnings may increase in volume as the drowsiness level increases. The tone can become one that is considered harsher when the drowsiness level increases. The spoken warning my use more severe language when the drowsiness level increases. In the case of vibrational warnings, the magnitude of the vibration may increase with an increase in the drowsiness level increases. The pulse pattern for the vibrations may change when the drowsiness level increases. Other warning changes may be used based on the level of drowsiness.

After the warnings are issued at an appropriate level (309), the process can return detecting drowsiness, e.g., with new data from the monitoring of the driver 301.

After drowsiness is detected, the process also moves from step 305 to step 311 where the detection distances of the collision warning systems can be increased or the time buffers can be decreased. The LIDAR/RADAR detection range can be increased. The external camera range can be increased. Increasing the range of detection allows the systems to detect objects farther away from the vehicle and allows more time to automatically process to compensate for the distracted state of the driver. The decrease of the time buffers reduces the time to impact and will cause the vehicle to activate collision avoidance systems sooner when the driver is distracted. The change in the detection range and/or the time parameters is based on the level of drowsiness detected.

At 313, the controller in the vehicle determines if a collision with a detected object is imminent. This can use the data from the detection systems, e.g., RADAR, LIDAR and images. If no imminent crash is detected, then the process moves to 318. If an imminent collision is detected, then the process moves to 317.

At 317, the collision warning systems and collision avoidance systems are engaged to warn and reduce to the impact of the imminent collision. If a collision does not occur, then the process returns to step 301.

Figure 4:
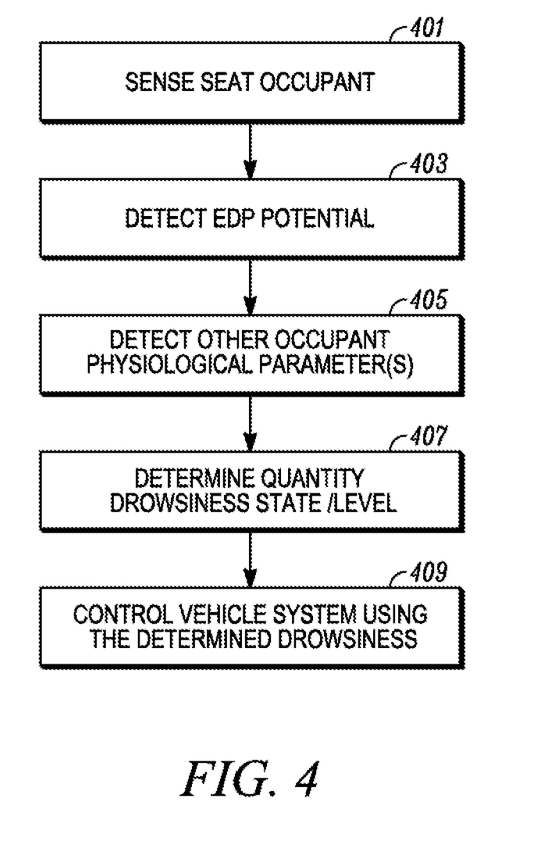
FIG. 4 is a chart of false drowsiness detection according to an example embodiment.

FIG. 4 shows a process 400 for detecting and quantifying drowsiness of a seat occupant, especially a driver of a vehicle. The process 400 can be implemented in the vehicle 100 in an example embodiment. At 401, occupancy of the vehicle seat is detected and the process of detecting the occupant's drowsiness begins. Occupancy can be detected using the sensor 156 to detect a weight in the range of a person in the seat. The occupancy can also be determined by an internal camera or the vehicle ignition being on and the vehicle in motion.

At 403, the electro-dermal potential of the seat occupant is detected. The EDP can be detected using contactless sensors that are in the seat and closely adjacent the seat occupant. The sensors can be adjacent the head of the seat occupant. The sensors can be adjacent the body of the occupant. The electro-dermal potential can be used to indicate the drowsiness of the occupant. The various signals can quantify drowsiness, e.g., a level of drowsiness.

At 405, a secondary physiological parameter of the occupant is sensed. In an example, the secondary physiological parameter can be the heart rate of the occupant. In an example, the secondary physiological parameter can be a respiration rate. In an example, the secondary physiological parameter can be heart rate variability (HRV). In an example, the secondary physiological parameter can be Cardiorespiratory Coupling/Synchrogram (CRS). The sensors to sense secondary physiological parameter can be in the seat.

At 407, the drowsiness state or the drowsiness level is determined. A controller processor receives the electro-dermal potential and the secondary physiological signal to determine the drowsiness state of the seat occupant or a drowsiness level of the seat occupant.

At 409, the drowsiness state or the drowsiness level is used to control vehicle systems. The vehicle systems can be safety systems, e.g., imaging systems, adaptive braking, collision avoidance, collision warning and the like. The safety systems may include time factors that are used to trigger an automated decision of an impending collision. The time factors may be based in part on the vehicle speed and the predicted reaction time of the driver. The reaction time of the driver may be increased as the drowsiness level increases or passes a drowsiness threshold. The time factors may also be adjusted based on the drowsiness level. As the drowsiness level increases, the time before the vehicle safety features will deploy are reduced in an attempt to reduce the likelihood of a collision.

The drowsiness state may be compared to a drowsiness threshold that when passed moves the vehicle from manual driving to an autonomous driving mode. In manual driving mode, the vehicle is controlled by the driver. In autonomous driving mode, the vehicle takes over most, if not all, of the driving tasks, e.g., speed, steering, braking and the like.

The drowsiness state or drowsiness level may be displayed in a heads-up display in an example embodiment. The heads-up display may be projected onto a windshield of the vehicle in the line of sight of the seat occupant. The heads-up display may show different icons to represent different drowsiness levels.

The control of vehicle systems 409 can also include calibrating the time factors based on historical records of drowsiness levels for a particular driver in the vehicle seat. The past drowsiness levels can be stored and analyzed to predict likelihood of current drowsiness levels.

Historical long-term data related to detected drowsiness can be processed secondarily to the real-time algorithms to provide a variety of statistical information for both the occupant and machine learning systems. The long-term data may be stored in the vehicle or off-vehicle. The vehicle may include electronic communication to an external server, e.g., over WiFi, mobile communication networks, such as cellular communications, and the like. The long-term drowsiness calculations may be used to alter the instructions for determining drowsiness or for mitigating false positives. The present disclosure quantifies the drowsiness/concentration status of the driver while correcting for false indications of drowsiness. The vehicle can use the drowsiness/concentration status of the driver to manipulate reaction times of various vehicle safety systems, e.g., the adaptive braking system, to optimize the response of the system itself. This may reduce the risk of forward collisions.

The present system can be used in an autonomous vehicle, e.g., a level 3 automobile, the vehicle needs to know the level of drowsiness, to be able to judge the most appropriate time to switch from manual to autonomous drive and vice-versa.

While the present vehicle is schematically illustrated as a passenger vehicle, the disclosure is not so limited. The vehicle for purposes of this disclosure include trucks, tractors, vans, boats, vessels, busses, trains, airplanes, mobile farm equipment, motorcycles, and the like. The drowsiness detection and quantification systems and methods described herein can be adapted to any of these vehicles, even beyond automotive and personal vehicles.

One example of electro-dermal potential may be electroencephalography (EEG), which is an electrophysiological monitoring method to record electrical activity of the brain. It is typically noninvasive, with the electrodes placed along the scalp, although invasive electrodes are sometimes used in specific applications. EEG measures voltage fluctuations resulting from ionic current within the neurons of the brain. In clinical contexts, EEG refers to the recording of the brain's spontaneous electrical activity over a period of time, as recorded from multiple electrodes placed on the scalp. Diagnostic applications generally focus on the spectral content of EEG, that is, the type of neural oscillations that can be observed in EEG signals.

The present disclosure is directed to a vehicle system that can detect drowsiness of an occupant in a vehicle seat. Drowsiness can be a feeling of being sleepy and lethargic or sleepiness, without actually falling asleep. In another example, sleeping is the extreme end of drowsiness. The examples used herein can quantify drowsiness up to sleeping. Drowsiness results in increased reactions time for a driver to respond to driving conditions. When the occupant is sleeping, then their drowsiness level would be 100%. In the case of sleeping, a vehicle with autonomous capabilities would lake over the driving of the vehicle. Many of the embodiments herein are directed to detecting levels of drowsiness short of sleeping. This will allow the vehicle systems to activate drowsiness indicators or alarms to alter the driver of their current state. The vehicle systems can also alter the factors, e.g., time parameters and detection distances, to alert the driver to a potential hazard early that normal.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system, comprising:
   an electro-dermal potential sensing system configured to sense electro-dermal potential of a person and configured to output an electro-dermal potential signal, wherein the electro-dermal potential system includes a plurality of contactless sensors configured to be mounted in a vehicle;
   at least one physiological sensor configured to measure at least one physiological state of the person and output at least one physiological signal; and
   a controller configured to receive the electro-dermal potential signal from the electro-dermal potential sensing system and the at least one physiological signal and to determine a drowsiness state of the person, wherein the controller is configured to adjust operation of a vehicle system using the determined drowsiness state, and wherein the controller is further configured to receive an external sensor signal from a vehicle environmental sensor system configured to sense external objects around a vehicle and to output a control signal using the electro-dermal potential signal, the at least one physiological signal and the external sensor signal to adjust operation of the vehicle environmental sensor system in the vehicle.

2. A system as recited in claim 1, further comprising:
   a vehicle seat;
   wherein said person is a driver seated in said seat; and
   wherein said electro-dermal potential sensing system is at least partially integrated into the seat.

3. A system as recited in claim 1, wherein said at least one physiological state includes at least one of breathing rate, heart rate variability, and Cardiorespiratory Coupling/Synchrogram (CRS).

4. The system of claim 2, wherein the control signal is to adjust operation of an adaptive braking system in the vehicle based on the determined drowsiness state of the driver exceeding a drowsiness threshold.

5. The system of claim 2, wherein the plurality of contactless sensors are configured to be mounted in the seat; wherein the seat includes a head rest, and wherein the plurality of contactless sensors includes one or more headrest sensors configured to be mounted in the headrest to measure electro-dermal potential at a head of the driver.

6. The system of claim 2, wherein the seat includes a driver warning device configured to indicate to the driver that the control signal representing drowsiness is output from the controller.

7. The system of claim 2, wherein the controller is configured to measure driver drowsiness based on individual frequency components in the electro-dermal potential signal.

8. The system of claim 2, wherein the controller is configured to quantify a drowsiness state level based on the electro-dermal potential signal and the physiological signal and to output a level signal to adjust a time-to-impact variable in an object avoidance calculation.

9. The system of claim 8, further comprising a camera configured to capture an image of the driver and produce a video output, and wherein the controller is configured to detect drowsiness indicators based on the video output, and wherein the controller is configured to calculate the drowsiness state level of the driver based on the drowsiness indicators.

10. The system of claim 2, wherein the controller is configured to quantify a drowsiness state level based on both the electro-dermal potential signal and the physiological signal and to control a driver alert based on the drowsiness state level, wherein the controller is configured to activate a driver alarm or a vibration in the seat in response to the drowsiness state level exceeding the drowsiness threshold.

11. The system of claim 2, wherein the vehicle environmental sensor system comprises an external sensor configured to detect objects external to the vehicle, the external sensor producing object detection signals using a sensor range, and wherein the controller is configured to increase the sensor range in response to the drowsiness state exceeding a drowsiness threshold.

12. The system of claim 2, wherein the controller is configured to receive at least one of an internal video signal, an external camera signal, a navigational position signal, and a vehicle speed signal, and wherein the controller is configured to determine a false drowsiness state of the driver based on the at least one of the internal video signal, the external camera signal, the navigational position signal, the vehicle speed signal and the electro-dermal potential signal.

13. The system of claim 2, wherein the controller is configured to switch the vehicle operation from a manual mode to an autonomous driving mode.

14. A vehicle system, comprising:
   a vehicle environmental sensor system configured to sense external objects around the vehicle and output an external sensor signal;
   a seat configured to support an occupant and to be mounted in a vehicle;

a contactless electro-dermal potential system configured to be at least partially integrated into the seat and configured to output an electro-dermal potential signal;

at least one physiological sensor configured to measure at least one of a e respiration rate, heart rate variability, and Cardiorespiratory Coupling/Synchrogram (CRS) of the occupant in the seat and to output at least one physiological signal indicative thereof; and a controller configured to receive the electro-dermal potential signal from the electro-dermal potential system, the at least one physiological signal and the external sensor signal from the vehicle environmental sensor system and to output a control signal using the electro-dermal potential signal, the at least one physiological signal and the external sensor signal to adjust operation of the vehicle environmental sensor system in the vehicle.

15. The vehicle system of claim 14, wherein the electro-dermal potential system includes a plurality of contactless sensors configured to be mounted in the seat.

16. The vehicle system of claim 14, wherein the vehicle environmental sensor system includes a detection and ranging system with a range setting to sense objects outside the vehicle including a position and a range of an external object, wherein the external sensor signal includes the position and range of the external object, and wherein the controller is configured to adjust the range setting based on the electro-dermal potential signal, the at least one physiological signal and the external sensor signal.

17. The vehicle system of claim 16, wherein the vehicle environmental sensor system includes a light sensor, a LIDAR sensor, a camera, a radio frequency sensor, or a RADAR sensor.

18. The vehicle system of claim 14, further comprising a collision avoidance system having a trigger time based on a control signal from the controller indicative of a drowsiness state of the occupant, wherein the collision avoidance system is configured to trigger an avoidance action based on the trigger time, wherein the collision avoidance system has a first trigger time in response to the control signal indicating a drowsiness state is not detected, a second trigger time in response to the drowsiness state exceeding a first level, and a third trigger time in response to the drowsiness state exceeding a drowsiness threshold, wherein the second trigger time is less than the first trigger time, and wherein the third trigger time is less than the second trigger time and the first trigger time.

19. A system, comprising:
an electro-dermal potential sensing system including a plurality of contactless sensors configured to sense electro-dermal potential of a person seated in a driver seat of a vehicle, the electro-dermal sensing system configured to output an electro-dermal potential signal;

at least one physiological sensor configured to measure at least one physiological state of the person and output at least one physiological signal; and a controller configured to receive the electro-dermal potential signal from the electro-dermal potential sensing system and the at least one physiological signal and to determine a drowsiness state of the person;

wherein the controller is further configured to adjust operation of an adaptive braking system in a vehicle based on the determined drowsiness state exceeding a drowsiness threshold, and wherein the controller is further configured to receive an external sensor signal from a vehicle environmental sensor system configured to sense external objects around the vehicle and to output a control signal using the electro-dermal potential signal, the at least one physiological signal and the external sensor signal to adjust operation of the vehicle environmental sensor system in the vehicle.

20. The system as recited in claim 19, wherein said at least one physiological state includes Cardiorespiratory Coupling/Synchrogram (CRS).

* * * * *

UNITED STATES PATENT AND TRADEMARK OFFICE
CERTIFICATE OF CORRECTION

PATENT NO. : 10,379,535 B2
APPLICATION NO. : 15/792085
DATED : August 13, 2019
INVENTOR(S) : Francesco Migneco et al.

It is certified that error appears in the above-identified patent and that said Letters Patent is hereby corrected as shown below:

In the Claims

Column 11, Lines 4-5, Claim 14:
After "at least one of a"
Delete "e".

Signed and Sealed this
Twenty-fifth Day of February, 2020

Andrei Iancu
*Director of the United States Patent and Trademark Office*